United States Patent [19]
Gordon

[11] Patent Number: 5,954,860
[45] Date of Patent: Sep. 21, 1999

[54] INDUCTIVELY HEATED COLD-TRAP ANALYTE INJECTOR

[75] Inventor: Gary B. Gordon, Saratoga, Calif.

[73] Assignee: Hewlett-Packard Company, Palo Alto, Calif.

[21] Appl. No.: 08/956,378

[22] Filed: Oct. 23, 1997

[51] Int. Cl.$^6$ .................................................. B01D 15/08
[52] U.S. Cl. .................................. 95/87; 95/89; 96/102; 96/105
[58] Field of Search ................................. 95/82, 87, 89; 96/101, 105

[56] References Cited

U.S. PATENT DOCUMENTS

| | | | |
|---|---|---|---|
| 3,057,183 | 10/1962 | Ford | 96/105 X |
| 3,146,616 | 9/1964 | Loyd | 95/87 X |
| 3,225,521 | 12/1965 | Burow | 95/87 X |
| 3,578,757 | 5/1971 | Samuilov et al. | 95/87 X |
| 4,035,168 | 7/1977 | Jennings | 95/87 X |
| 4,422,860 | 12/1983 | Feinstein | 95/89 X |
| 4,650,964 | 3/1987 | Vincent | 95/87 X |
| 4,728,776 | 3/1988 | Vincent | 95/87 X |
| 4,923,486 | 5/1990 | Rubey | 95/87 |
| 5,028,243 | 7/1991 | Rubey | 95/87 |
| 5,096,471 | 3/1992 | Sacks et al. | 95/87 |
| 5,135,549 | 8/1992 | Phillips et al. | 95/87 X |
| 5,141,532 | 8/1992 | Sacks et al. | 95/87 |
| 5,215,556 | 6/1993 | Hiller et al. | 95/87 |
| 5,252,109 | 10/1993 | Munari et al. | 95/87 |
| 5,588,988 | 12/1996 | Gerstel et al. | 96/101 |
| 5,720,798 | 2/1998 | Nickerson et al. | 96/105 X |

OTHER PUBLICATIONS

B.A. Ewels and Robert D. Sachs in "Electrically Heated Cold Trap Inlet System for High–Speed Chromatography", American Chemical Society, 1985, pp. 2274–2279.

Mark A. Klemp, Michael L. Akard, and Robert D. Sachs, in "Cryofocusing Inlet with Reverse Flow Sample Collection for Gas Chromatography", American Chemical Society, 1993, pp. 2516–2521.

*Primary Examiner*—Robert Spitzer

[57] ABSTRACT

An injector for a gas chromatography system resistively heats an included cold trap by magnetically inducing a high-frequency current therethrough to inject absorbed analyte into a gas chromatography separation column. The injector includes a flow controller that is set initially to load analyte into the trap. A heater and a two-stage Peltier cooler are used to establish a sharp trough-shaped temperature gradient along the cold trap so that analyte loaded into the cold trap is absorbed only at a relatively cold "focussing" zone of the trap. Once the analyte is focussed, the flow controller is set to direct released analyte into the column. The magnetic-field generator includes a capacitor that is discharged to initiate cold-trap heating. An inverter converts the discharge to a 100,000 Hz waveform through a transformer primary coil. A magnetic core delivers the resulting alternating magnetic field through the cold trap. The resulting AC current resistively heats the cold trap, volatizing analyte components so that they are injected into a gas chromatography column. The relatively modest power requirements for this compact arrangement provide for a practical cold-trap injector so that higher spatial resolution and greater effective sensitivity are achieved in the context of small-bore gas chromatography.

14 Claims, 5 Drawing Sheets

INDUCTIVELY HEATED COLD-TRAP ANALYTE INJECTOR

BACKGROUND OF THE INVENTION

The present invention relates to analytical chemistry and, more particularly, to gas chromatography. A major objective of the invention is to provide an improved flash injector for a gas chromatography system.

Analytical chemistry has advanced human and environmental health by permitting the components of, for example, medical and environmental samples to be separated for detection, identification, and quantification. Gas chromatography, an increasingly important separation method, separates vaporized analyte components according to their different partitionings between a mobile and a stationary phase.

In a typical gas chromatography system, the tubular column is packed or internally coated with material that differentially absorbs analyte components. As analyte molecules flow past the absorbent material, they are alternately absorbed by it and adsorbed back into the carrier gas. Each component achieves an equilibrium at which the rate of absorption equals the rate of adsorption so that the percentage of molecules that are absorbed remains constant. The higher the percentage of a component's molecules that are absorbed, the slower the component migrates down the column. Thus, the components progressively separate according to their partitioning constants. Once separated, the components can be individually detected and/or collected for further analysis.

The molecules associated with a particular component do not all elute from the column at the same instant; instead, the molecules are distributed around a peak. If the column is unable to provide sufficient separation (spatial resolution) between two components, the distributions overlap. The overlap makes it more difficult to quantify the components and to collect them individually.

One method of increasing spatial resolution is to use a longer column so components have more time to separate. However, the gain in resolution is partially offset by the additional spreading that occurs in the extra time. Moreover, the longer separation time decreases analytical throughput. The optimizing column length is a practical tradeoff between increased separation and these negative results. Given that column length is readily optimized, further improvements require other approaches to improving spatial resolution.

Decreasing the inner diameter of the column can increase spatial resolution by shortening the average radial diffusion distance, which, in turn, reduces the standard deviation of elution time. Peaks are narrower and thus less prone to overlap. The additional resolution obtainable using a narrower column can be traded for a shorter column to reduce analysis time and increase analysis throughput.

The decreased column diameter limits the amount of analyte that can be injected for a given plug length. The amount of analyte is further limited since shorter plug lengths are desired for small-bore columns to take advantage of their potentially greater spatial resolution. The reduction in analyte reduces the amount of analyte available for detection. This effective reduction in instrument sensitivity has limited commercialization of small-bore columns, despite advantages in throughput and resolution.

Cold traps promise to address both the needs for reduced plug length and increased effective sensitivity for small-bore columns. A cold trap can be used to concentrate and focus an analyte on a cooled stationary phase prior to introduction to the column. Typically, a metal or glass cold trap is coated or packed with absorbent organic polymer. The packing slowly absorbs a flowed-through analyte, which is thereby concentrated. The cold trap can then be heated rapidly so that the analyte is flash-volatilized to produce a sharp plug of analyte for introduction into the column. In addition to improving resolution, the cold trap concentrates the components so that they are more readily detected, effectively increasing instrument sensitivity.

So that the focal region is well defined, the focal zone must be much more absorptive than adjacent zones of the cold trap. Even without organic absorptive material to trap it, analyte can condense outside the focussing zone, impairing the definition of the analyte plug to be injected onto the column. Heating the cold trap away from the focussing zone can prevent this condensation. Such heating can be achieved by interfacing the trap with a hot manifold so that the cold-trap ends are heated. In addition, the focussing zone can be cooled to increase its retentiveness. A sharply defined hot-cold-hot temperature gradient is preferred to minimize plug length.

Once the analyte is concentrated in the cold trap, the cold trap can be heated to release the trapped analyte into the column. To minimize plug spreading during release, the heating should be very rapid, e.g., from below ambient to hundreds of degrees Celsius above ambient in tens of milliseconds or less. A trap can be resistively heated by passing a large current therethrough to vaporize the analyte. For resistive heating, the cold trap must be conductive, thus excluding insulators such as glass as the trap wall material. Since a trap typically represents a low resistance, e.g., on the order of 10 milliohms, delivering the required current, e.g., hundreds of amperes, to provide the rapid heating has been problematic.

A system using transformers to generate large currents using 60 Hz power sources is disclosed by B. A. Ewels and Robert D. Sachs in "Electrically Heated Cold Trap Inlet System for High-Speed Chromatography", American Chemical Society, 1985, pp. 2274–2279. A transformer connected to a 208 Volt 60 Hz power source provides an initial rapid heating of a stainless-steel cold trap. Despite the great need for a gas chromatography system with a resistively heated cold trap, this system has not given rise to a commercially successful system. The lack of success can be attributed to the compromises required to draw sufficient power to heat the trap rapidly. In the present case, some of the compromises are: 1) a requirement for a higher-than-standard line voltage; 2) a large and expensive transformer; and 3) a requirement for line power.

An alternative gas-chromatography injector discharges a bank of capacitors through a cold trap, as disclosed by Mark A. Klemp, Michael L. Akard, and Robert D. Sachs, in "Cryofocusing Inlet with Reverse Flow Sample Collection for Gas Chromatography", American Chemical Society, 1993, pp. 2516–2521. The problem of extracting high power from an AC source is avoided since the AC power source is used merely to charge the capacitors. However, the cold trap represents only a small fraction of the circuit resistance of the discharge circuit (which includes silicon-rectifier switches). Thus, only a small fraction of the energy delivered by the capacitors is converted to heat at the cold trap. As a result, the capacitors must be able to hold many times the energy required for heating the cold trap. The bulk and expense of the required capacitors are impediments to a commercial realization.

A variation of the foregoing injector employs a thin-walled cold trap to increase trap resistance and reduce the required capacitance. However, the thin trap is unacceptably fragile and is prone to breakage. Another approach to reducing power requirements is to use a more resistive trap wall material. Nickel is a preferred trap wall material because of its chemical inertness. Stainless steel, used in the Ewel et al. system described above, has greater resistance. However, stainless steel is more reactive chemically than nickel, so use of stainless steel unacceptably limits the types of analytes that can be analyzed.

In the foregoing systems, the electrical conductors delivering current to the cold traps are thermally conductive; thus, they can conduct heat away from the trap ends; this can impair the sharpness of the thermal gradient along the trap required for establishing a short analyte plug. The conductors can be heated, but this can have adverse consequences as well. If the conductors are copper, the heat can oxidize them, increasing their resistivity. Other materials, e.g., nickel, oxidize less readily, but are more resistive to begin with. Attempts to use a transformer secondary as the conductor have been hindered by the current requirements for the primary and the size required of the transformer core.

Thus a long-standing need has existed for a commercially practicable cold-trap focusing-injector for gas chromatography, i.e., a system for introducing analyte into a gas-chromatography column that uses a cold-trap to concentrate the sample prior to injection. Such an injector would address the sensitivity limitations of prior art small-bore columns and help realize their potential for speedy, high-resolution, analyses.

SUMMARY OF THE INVENTION

The present invention provides for magnetically inducing a high-frequency (>500 Hz) alternating current in an electrically conductive loop including a cold-trap injector tube. In addition to the loop, the system includes a magnetic-field generator for generating an alternating magnetic flux through the loop and a flow controller for conveying analyte into and out of the trap. A heater can be used to heat the ends of the trap tube, while a cooler can be used to cool an intermediate focusing zone of the trap tube.

The magnetic field generator can include a primary coil, a high-frequency alternating current source for generating an AC current through the primary coil, and a core inductively coupled to the primary coil so that an alternating magnetic field is generated in the core. The current source preferable comprises a capacitor and an inverter for generating the AC current from the capacitor discharge. A sufficiently high frequency of alternation is selected so that the trap can be heated at a high power rate, and thus rapidly, without saturating the magnetic-generator core. Preferably, the frequency f in Hertz should be selected so that $3.5 < \log_{10} f < 5.5$. The loop is inductively excited by the core. In effect, the loop becomes a, preferably one turn, secondary winding of a transformer.

Preferably, the cold-trap itself is disposed directly within the alternating magnetic field. An electrically conductive manifold that physically and electrically couples to the two ends of the tubular trap can complete the secondary circuit. The manifold is preferably heated so as to serve as the heat source for the hot zones of the trap. Alternatively, a portion of the loop other than the trap tube can be disposed in the alternating magnetic field; in this case the alternating current is conducted to the tube walls.

The cooler can be interfaced to the cold trap tube through a thin layer of insulation. The insulation allows the tube to be heated rapidly without significant loss to the cooler without moving the cooler and the rap tube apart. The insulation is thin enough so that the tube cools effectively while not being resistively heated.

The method of the invention begins with establishing initial conditions. A suitable trough-shaped temperature gradient is established along the cold trap so that analyte is absorbed in a short intermediate cold "focal" zone of the cold trap; the temperature gradient can be established by cooling the focal segment and heating the trap ends. If the current source for the magnetic-field generator is a capacitor, it is charged. The flow controller is set so that analyte can flow into the trap.

The analyte can be ushered into the trap so that it is absorbed at the focal zone to define a short analyte plug. The flow controller is set to inject analyte into a gas-chromatography column. The magnetic-field generator is activated, inductively heating the cold trap so that the plug is volatilized and carried into the gas chromatography column. The analyte components are then separated by the column, and the separated components are detected. The separated and detected components can then be identified, quantified, collected, and further analyzed.

The invention combines seemingly conflicting AC and DC aspects of prior art approaches to resistive heating of a cold trap. As in Klemp et al, a transformer is used for impedance matching an AC power source to a conductive loop including a cold trap. As in Ewels et al., high instantaneous power is achieved by discharging a capacitor, rather than by drawing the required power in real time from a line source. To these aspects, the present invention adds an inverter to convert the capacitor discharge to a high-frequency alternating current that is inductively coupled to the conductive loop including the cold trap. This high-frequency alternation allows a vastly smaller transformer core to be used without being saturated. This, in turn, makes for a compact and economical injector.

Unlike some prior-art resistively heated cold-trap systems, the present invention does not necessitate compromising on tube material or thickness. Furthermore, no thick conductors are required to deliver the alternating current to the cold-trap tube that would otherwise impair the thermal gradient along the cold trap and dissipate energy away from the target cold trap. The layer of insulation between the cooler and the cold-trap tube provides a simple solution to the conflicting demands of rapid heating and effective cooling.

The present invention provides a practical realization of a resistively heated cold-trap injector for a gas chromatography system. The objectives of such a device is that a shorter analyte and more highly concentrated analyte plug is introduced into a column. Thus, shaper component peaks emerge during separation, practically achieving greater spatial resolution and effective sensitivity in the context of small-bore gas chromatography columns. The promise of small-bore gas chromatography is closer to realization providing a more sensitive tool for those striving for advances in individual and environmental health. These and other features and advantages of the invention are apparent from the description below with reference to the following drawings.

DESCRIPTION OF THE PREFERRED EMBODIMENTS

Figure 1:
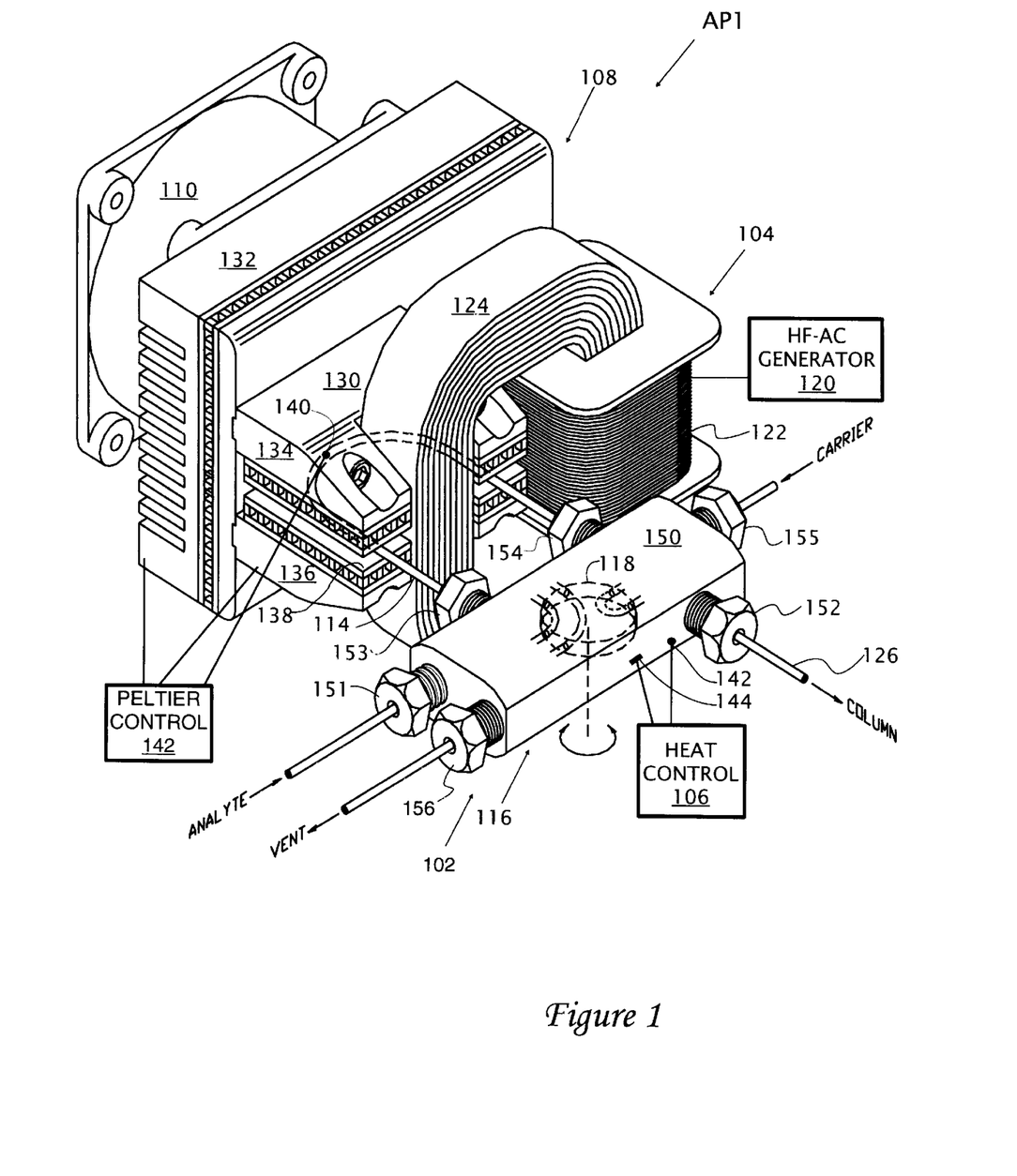
FIG. 1 is a perspective illustration of a resistively-heated cold-trap injector system for a gas chromatography system in accordance with the present invention.

A gas-chromatography injector AP1 in accordance with the present invention comprises: an analyte flow controller 102, a magnetic-field generator 104, a heater 106, a cooler 108, and a fan 110. Flow controller 102 comprises a tubular cold trap 114, a manifold 116, and a valve 118. Magnetic field generator 104 comprises an AC generator 120, a primary coil 122, and a magnetic core 124.

Two-stage Peltier cooler 108 comprises a first-stage Peltier cooler 130 and a second-stage Peltier cooler 132. The cool side of first-stage Peltier cooler 130 has an upper jaw 134 and a lower jaw 136 that cooperatively engage a length of cold-trap 114 through an insulating layer 138. The jaws are slotted to accommodate core 124. The cool side of second-stage Peltier cooler 132 is coupled to the hot side of first-stage cooler to remove heat therefrom. Fan 110 is coupled to the hot side of second-stage Peltier cooler 132 to remove heat convectively from therefrom.

A thermister 140, disposed near the longitudinal center of trap 114, monitors the trap temperature, which is thus communicated to a Peltier control 142. Peltier control 142 adjusts the currents through Peltier coolers 130 and 132 to maintain a cold trap temperature of about −20° C. under steady state conditions.

Insulating layer 138 is a mat of woven glass; its purpose is to retard heat removal sufficiently to permit rapid heating. The insulator retards heat removal sufficiently to permit ballistic heating of trap 114, while allowing trap 114 to cool to its steady-state temperature within a minute or so.

Manifold 116 has a machined nickel body 150 housing a temperature sensor 142 and a resistive heater 144. Measurements by sensor 142 are used by heat control 106 to regulate the temperature of manifold 116 by adjusting the current through resistive heater 144. Manifold 116 has six ports, an analyte input 151, an injection output 152, a trap-analyte port 153, a trap-carrier port 154, a carrier input 155, and a vent 156. Commonplace metallic compression ferrules engage the tubing both mechanically and electrically. The internal coupling is determined by the orientation of valve 118, which defines four flow paths, 202, 204, 206, and 208, as shown in FIG. 2.

Figure 2:
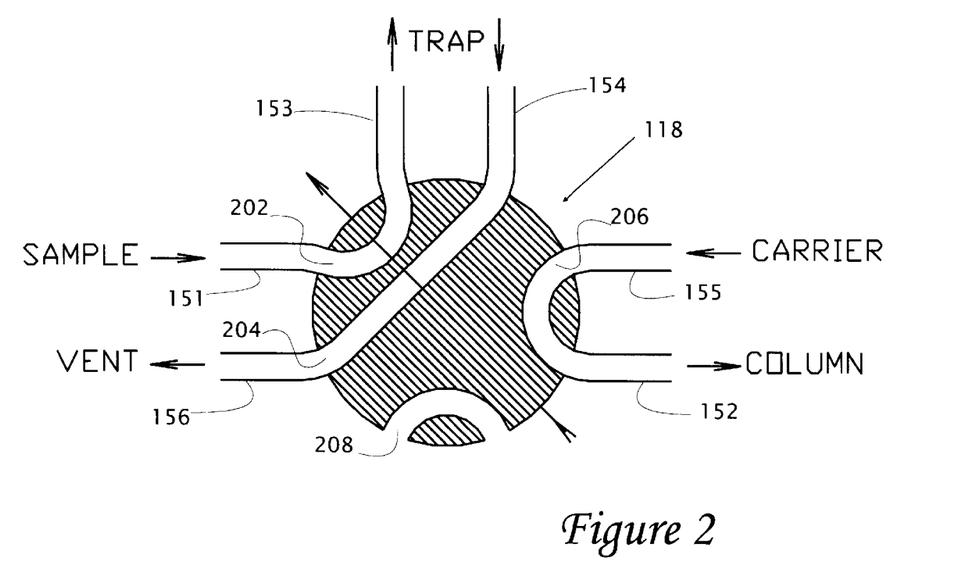
FIG. 2 is a schematic view of a valve in an analyte-load position for the injector system of FIG. 1.
Figure 3:
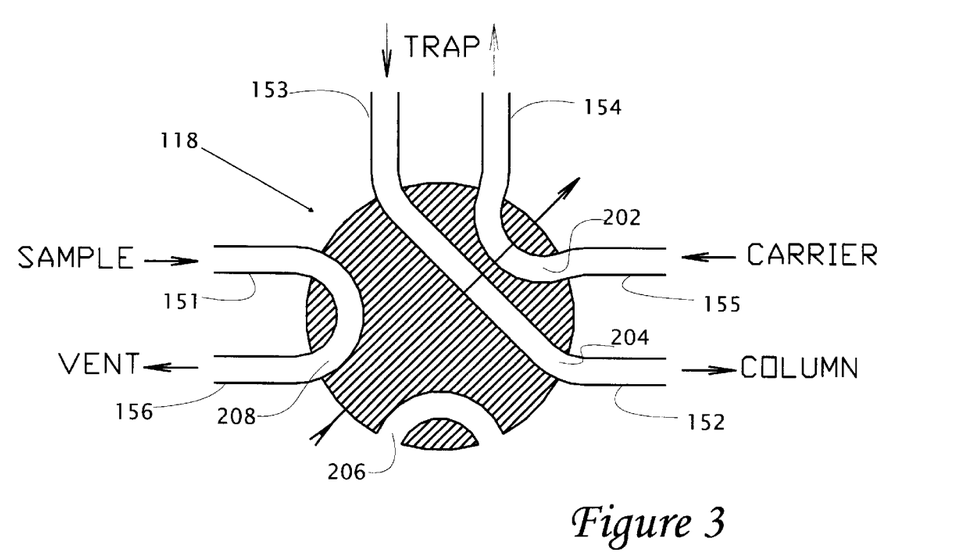
FIG. 3 is a schematic view of the valve of FIG. 2 in an analyte-inject position.

Valve 118 is shown in a "load" orientation in FIGS. 1 and 2. In this load orientation: flow path 202 directs analyte from analyte input 151 to trap-analyte port 153; flow path 204 directs gas displaced by analyte from trap-carrier port 154 to vent 156; flow path 206 directs carrier gas from carrier input 154 to analyte output 152 (coupled to column 126); and flow path 208 is not used. Valve 118 is shown in an "inject" orientation in FIG. 3. In this inject orientation: flow path 202 directs carrier gas from carrier input 155 to trap-carrier port 154; flow path 204 directs analyte from trap-analyte port 153 to injection output 152; flow path 208 directs any input to analyte input 151 to vent 156; and flow path 206 is not used.

Cold-trap 114 is a common thick-wall nickel tube that is about 5 cm long, about 810 microns ($\mu$m) in external diameter, and about 250 $\mu$m internal diameter. The length is selected to balance sensitivity and selectivity; the diameter is chosen for strength and availability. Cold-trap 114 is bent into a U-shape so that its ends respectively engage trap-analyte port 153 and trap-carrier port 154. The resistance of cold-trap 114 is about 0.0085 ohms ($\Omega$). Although not a high resistance, it is by far the larger portion of the resistance of the loop constituted by trap 114 and manifold 116, the latter presenting a much larger cross-section to current in the loop.

Figure 4:
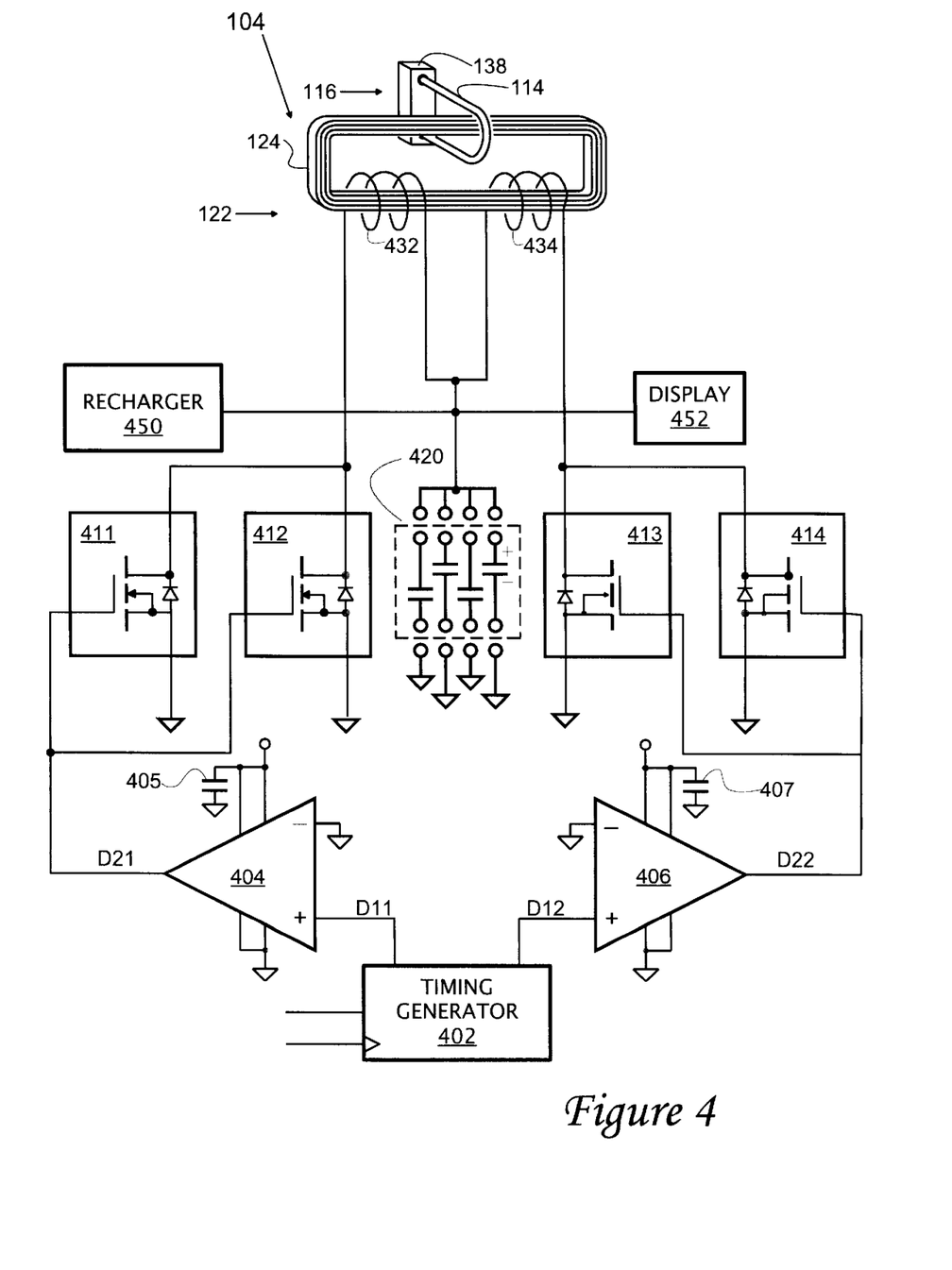
FIG. 4 is a circuit diagram of electrical and magnetic components of the injector system of FIG. 1.
Figure 5:
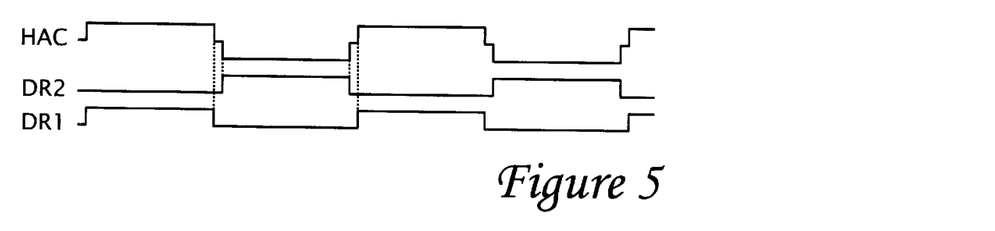
FIG. 5 is a timing diagram showing drive signals and the current waveform through a cold trap of the system of FIG. 1.

HF-AC generator 120 comprises a timing generator 402, differential amplifiers 404 and 406, field effect transistors 411–414, and a small bank of capacitors 420, as shown in FIG. 4. In addition, a recharging circuit 450 is used to charge capacitor bank 420, while a display 452 is used to indicate the charge level of capacitor bank 420. Timing generator 402 generates drive signals D11 and D12, which are generated one-half cycle out of phase. Each drive signal is basically a square wave with a duty cycle of about 49.9%. The less than 50% duty cycles are employed to ensure that both drive signals are never on at the same time.

Drive signals D11 and D12 are amplified by amplifiers 404 and 406 to yield amplified drive signals D21 and D22. Associated respectively with amplifiers 404 and 406 are 1.0 $\mu$F voltage-bypass capacitors 405 and 407.

Amplified drive signal D21 drives the gates of transistors 411 and 412 so that they conduct while and only while drive signal D21 is high; while transistors 411 and 412 are conductive, charge stored in capacitor bank 420 can discharge through a first half coil 432 of primary c oil 122. Amplified drive signal D22 drives the gates of transistors 413 and 414 so that they conduct while and only while drive signal D22 is high; while transistors 413 and 414 are conductive, capacitor bank 420 can discharge through a second half coil 434 of primary coil 122.

Capacitor bank 420 comprises four 0.022 micro-Farad ($\mu$F) capacitors, for a total capacitance of 0.088 $\mu$F. The voltage differential across capacitor bank 420 during recharge is 48 Volts. Thus, capacitor bank 420 can store about 90–100 Joules.

Half coils 432 and 434 are 18-gauge litz wires wound around core 124 eight times each. Half coils 432 and 434 are respectively wound so that the magnetic field induced in core 124 when capacitor bank 420 discharges through half coil 432 is opposite to the magnetic field induced in core 124 when capacitor bank 420 discharges through half coil 434. Referring now to FIG. 1, the resulting alternating magnetic field through core 124 extends through cold trap 114 so that an alternating current is generated through flow controller 102 (including trap 114).

Core 124 is formed of tape wound thin 0.0001" grain-oriented nickel steel. Core 124 handles 5000 lines of flux per square centimeter before saturation. The maximum secondary voltage that can be achieved without saturating core 124 is 9 volts at 100 kHz. The maximum secondary voltage varies linearly with frequency, so a tradeoff may be made between power handling capacity and core efficiency.

Figure 6:
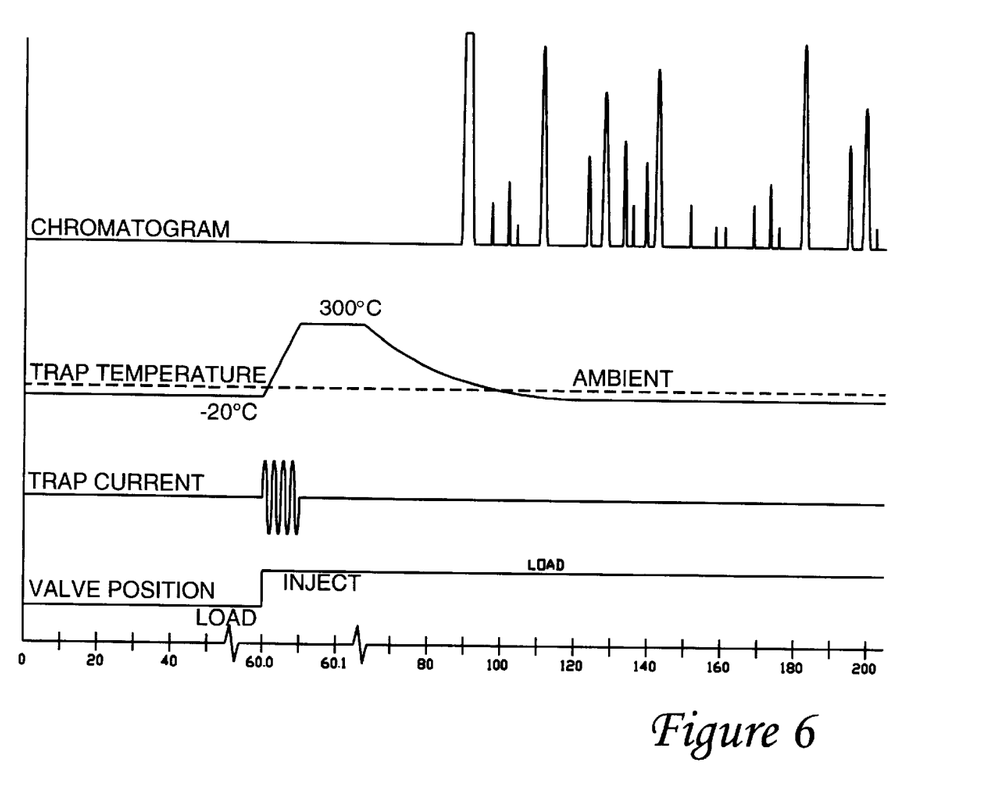
FIG. 6 is a graph showing the variation of selected parameters over time for the system of FIG. 1.

Energy is dissipated by cold trap 114 and by manifold 118 as the alternating current flows through both. However, due to the relatively large cross section presented by the manifold to the current, at least 90% of the energy dissipated by flow controller 102 is dissipated by cold trap 114. As a result, the temperature of cold trap 114 rises rapidly from −20° C. to 300° C. in about 10 ms. The relationship between the alternating current and the heating is depicted in the graph of FIG. 6.

Figure 7:
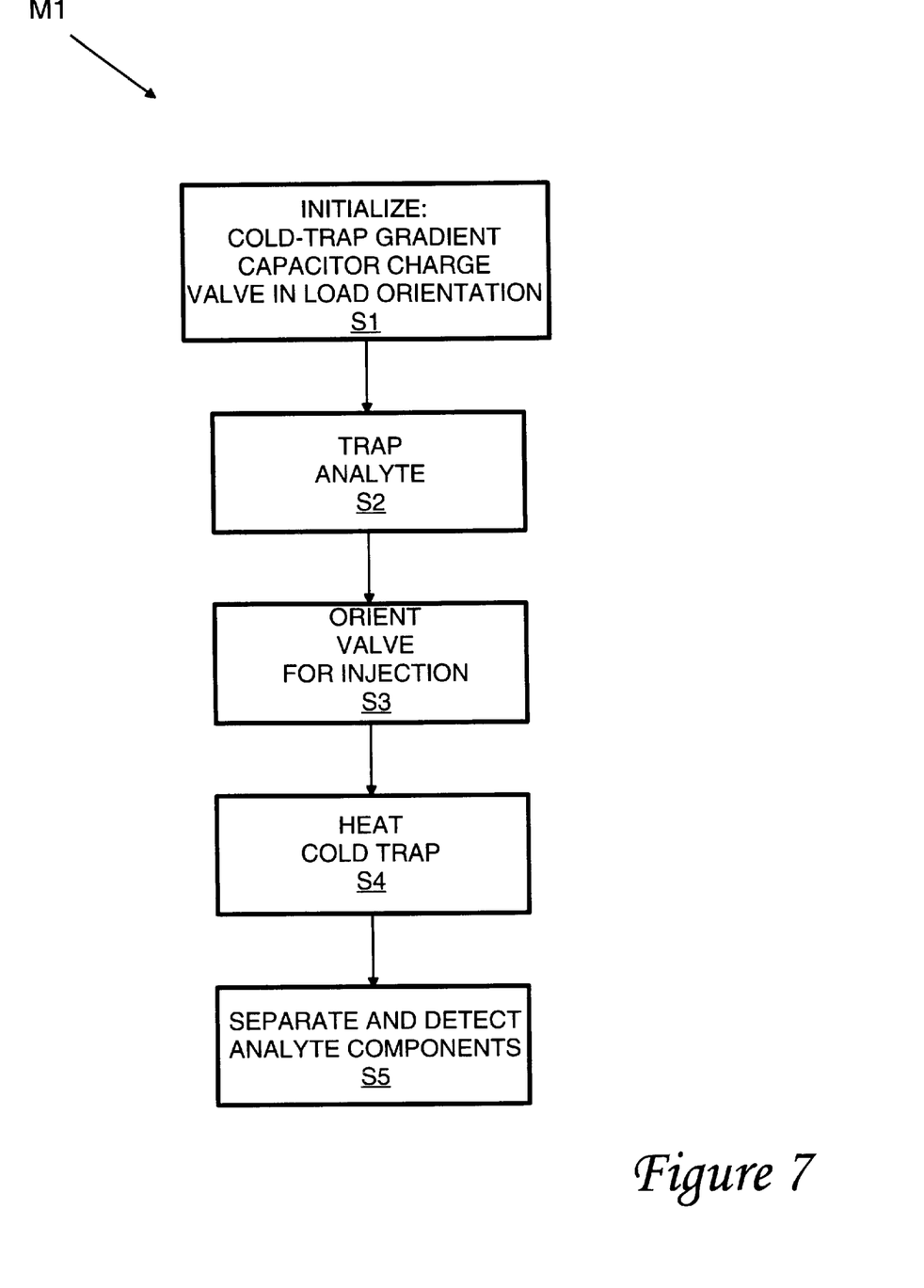
FIG. 7 is a flow chart of a method of the present invention practiced in the context of the system of FIG. 1.

A method M1 implemented in the context of gas-chromatography injection system AP1 is flow charted in FIG. 7. At step S1, initial conditions are established. Cooler 108 maintains the portion of cold trap 114 within the jaws of first Peltier cooler 130 is maintained below ambient temperature, while heater 106 maintains manifold 116 at an elevated temperature. Valve 118 is in the load orientation of FIG. 2 so that the carrier gas is directed through column 126. Capacitor bank 420 is fully charged.

At step S2, analyte is trapped in cold-trap 114. Analyte, entrained in a carrier gas, is introduced into flow controller 102 via analyte input 151. The analyte flows through heated manifold 140, but is readily absorbed by cooled cold trap 114. At step S3, shortly before the injection phase, valve 118 is pneumatically rotated to its inject position, FIG. 3. This routes carrier gas through cold trap 114 (which is still cold) and onto column 126. However, analyte is not released from cold trap 114 until it is flash heated.

At step S4, magnetic-field generator 104 is activated so that an alternating magnetic field is generated through said loop and encircling said trap tube so that a high-frequency current is generated through analyte flow controller 102. If the temperature of column is to be ramped, the ramp can begin just before activation of magnetic-field generator 104. The resistance of cold trap 114 converts the current to heat at about 40,000° C. per second. A temperature of 300° C. is achieved in 10 ms; this temperature is sufficient to release most analyte components. Higher temperatures can be achieved, but should be sufficiently limited to avoid damage to the cold-trap coating. At this point, a plug of concentrated analyte less than 10 ms is launched into separations column 126.

At step S5, volatilized analyte components are separated along column 126, resulting in a chromatogram as indicated in FIG. 6. In preparation for a next iteration of method M1, capacitor bank 420 is recharged and valve 118 is rotated to its load position. Once cold trap 114 is restored to its initial subambient temperature, a new iteration of method M1 can begin.

In effect, the invention involves a specialized transformer in which the cold trap serves as a single-turn secondary winding. Accordingly, the present invention provides for embodiments that incorporate known and yet-to-be-known substitutes for elements of the preferred embodiment. Any magnetic system common to transformer-style switching regulator power supplies, including ferrite core transformers can be readily adapted. A bank of capacitors drives the transformer primary; in other embodiments, a transformer can be driven by rectified and, optionally, filtered line voltage, much as present day switching regulators are. Alternatively, the injector can be powered from an unregulated power supply such as the oven supply, already incorporated into the gas chromatography system. In this case, the oven can be disabled momentarily during the injection moment so that the supply demands of the injector and oven are not additive.

The invention requires that a conductive loop including the cold-trap be excited inductively. In the preferred embodiment, the cold trap itself is encircled by an alternating magnetic flux. Alternatively, the manifold can be situated within an alternating magnetic flux. More generally, other conductors included within the loop can be inductively excited.

In the preferred embodiment, the heat is removed from the second-stage Peltier cooler by a fan. Alternative embodiments use other convective cooling means, for example, a water-based heat exchanger. In the preferred embodiment, Peltier cooling is employed. Alternative embodiments can use cryogenic cooling. Various types of temperature sensors can be used instead of a thermister for heat monitoring and regulation; for example, some embodiments include a platinum resistance thermometer to measure and to regulate the cold and the hot temperatures of the trap.

The preferred embodiment employs woven glass as an insulator between the trap and the cooler. Alternatively, another refractory material can be used for retarding thermal transfer. Another alternative is to employ movable Peltier jaws, which can thus be disengaged during ballistic heating. These and other variations upon and modifications to the preferred embodiments are provided for by the present invention, the scope of which is limited only by the following claims.

What is claimed is:

1. An analyte injection method comprising:

introducing analyte into a conductive trap tube with analyte-absorbing material in its interior;

generating an alternating electric current through said trap tube by generating an alternating magnetic flux through an electrically conductive loop including said trap tube so as to heat said trap tube, said magnetic flux and said current having a common frequency f in excess of 500 kHz; and conveying analyte released by the heating of said trap tube into a gas chromatography column.

2. A method as recited in claim 1 wherein said step of generating an alternating magnetic flux involves generating said magnetic flux so that it encircles said trap tube.

3. A method as recited in claim 1 further comprising a step of, before said introducing step, establishing a temperature gradient along said trap tube.

4. A method as recited in claim 3 wherein said establishing step involves insulating said trap tube from a cooler to facilitate rapid heating of said trap tube during said generating step.

5. A method as recited in claim 1 wherein $3.5 < \log_{10} f < 5.5$.

6. An analyte injection method comprising:

introducing analyte into a conductive trap tube with analyte-absorbing material in its interior;

discharging a capacitor to generate a direct current;

converting said direct current to a primary alternating current through a primary coil;

transforming said primary alternating current through to a secondary alternating current through a conductive loop including said conductive trap tube so as to cause heating of said conductive trap tube; and conveying analyte released by said heating into a gas chromatography column.

7. A cold-trap focusing trap system for injecting an analyte into a chromatography column, said system comprising:

an electrically conductive injector loop including a conductive trap tube having material therein for absorbing said analyte;

a magnetic-field generator for generating an alternating magnetic flux through said electrically conductive loop so as to generate an alternating trap current therein so as to heat said conductive trap tube, said alternating magnetic flux and said alternating trap current having a common frequency f greater than 500 Hz; and an analyte flow controller for admitting said analyte into said trap tube and for conveying said analyte from said trap tube to said chromatography column when said trap tube is heated.

8. A system as recited in claim 7 wherein said conductive trap tube is disposed within said alternating magnetic flux.

9. A system as recited in claim 7 wherein said magnetic-field generator includes an alternating current generator, a primary coil electrically connected to said alternating current generator, and a magnetic core magnetically coupled to said primary coil, said magnetic core being magnetically coupled to said electrically conductive injector loop for inducing said alternating trap current therein.

10. A system as recited in claim 7 wherein said trap tube primarily consists of nickel.

11. A system as recited in claim 7 further comprising a temperature controller for establishing a temperature gradient along said trap tube.

12. A system as recited in claim 11 further comprising:

a cooler for cooling said trap tube; and thermal insulating material between said cooler and said trap tube so that said trap tube can be heated relatively rapidly and cooled relatively slowly.

13. A system as recited in claim 7 wherein $3.5<\log_{10}f<5.5$.

14. A cold-trap focusing trap system for injecting an analyte into a chromatography column, said system comprising:

an electrically conductive injector loop including a conductive trap tube having material therein for absorbing said analyte;

capacitor means for generating a current;

inverter means for converting said current to a first alternating current;

transformer means for converting said first alternating current into a second alternating current along said electrically conductive injector loop; and an analyte flow controller for admitting said analyte into said trap tube and for conveying said analyte from said trap tube to said chromatography column when said trap tube is heated.

* * * * *